(12) United States Patent
Eguchi et al.

(10) Patent No.: US 8,477,186 B2
(45) Date of Patent: Jul. 2, 2013

(54) APPARATUS FOR REMOVING REFLECTED LIGHT

(75) Inventors: Hirotsugu Eguchi, Tokyo (JP);
Mitsuhiko Matsumoto, Tokyo (JP)

(73) Assignee: Sumco Corporation, Tokyo (JP)

( * ) Notice: Subject to any disclaimer, the term of this patent is extended or adjusted under 35 U.S.C. 154(b) by 480 days.

(21) Appl. No.: 12/751,045

(22) Filed: Mar. 31, 2010

(65) Prior Publication Data

US 2010/0253776 A1 Oct. 7, 2010

(30) Foreign Application Priority Data

Apr. 6, 2009 (JP) .................................. 2009-091787

(51) Int. Cl.
*H04N 7/18* (2006.01)
*G01N 21/00* (2006.01)

(52) U.S. Cl.
USPC ............ 348/135; 356/335; 356/336; 356/640

(58) Field of Classification Search
USPC .................. 348/135, 127; 356/335, 336, 640
See application file for complete search history.

(56) References Cited

U.S. PATENT DOCUMENTS

| | | | |
|---|---|---|---|
| 5,686,996 A * | 11/1997 | Fidler et al. | 356/399 |
| 5,841,534 A * | 11/1998 | Lorenz | 356/336 |
| 6,859,277 B2 * | 2/2005 | Wagner et al. | 356/337 |
| 2002/0045276 A1 * | 4/2002 | Yguerabide et al. | 436/518 |
| 2005/0167621 A1 * | 8/2005 | Zeng et al. | 250/580 |

FOREIGN PATENT DOCUMENTS

| | | |
|---|---|---|
| JP | 9-089755 | 4/1997 |
| JP | 2005-140740 | 6/2005 |

* cited by examiner

*Primary Examiner* — Anner Holder
(74) *Attorney, Agent, or Firm* — Greenblum & Bernstein, P.L.C.

(57) ABSTRACT

An apparatus for removing reflected light is provided, which is used for a measuring device that emits a sheet-like beam of light onto suspended particles and measures light scattered from the suspended particles. The apparatus includes a light introduction unit, a light reflective unit, a light sealing unit and a light absorption member. The light introduction unit has a first aperture, a second aperture, and a passage through which the light travels from the first aperture to the second aperture. The light reflective unit disposed opposite to the second aperture allows the light having traveled through the second aperture to reflect toward a predetermined direction so as to prevent the light from returning into the second aperture. The light sealing unit in which the light reflective unit is disposed has an inner wall to confine the light reflected from the light reflective unit.

8 Claims, 5 Drawing Sheets

APPARATUS FOR REMOVING REFLECTED LIGHT

This application is based on and claims the benefit of priority from Japanese Patent Application No. 2009-091787, filed on 6 Apr. 2009, the content of which is incorporated herein by reference.

BACKGROUND OF THE INVENTION

1. Field of the Invention

The present invention relates to an apparatus for removing reflected light. The present invention particularly relates to an apparatus for removing reflected light that is used for implementing visualization of particles suspended in the air with high sensitivity.

2. Related Art

In a factory manufacturing or employing paints, foods, films, liquid crystals, semiconductors and the like, particles suspended in the air (suspended particles) are monitored constantly, periodically or irregularly, thereby preventing unnecessary particles from contaminating or adhering to a product.

Since it is impossible to observe with the naked eye the suspended particles that have small diameters, it is difficult for a person to know the cleanliness of a room without an instrument. In order to solve such a difficulty, a measuring device has been proposed that observes or records suspended particles visualized by light projection.

As an example of such a detection device is disclosed, which includes a light source, a light receiving element, a sheet of black paper and a detection circuit. The light receiving element detects light reflected from particles suspended in an area irradiated with light from the light source. The sheet of black paper is disposed on the extension of an axis line defined for a light receiving portion of the light receiving element. The detection circuit detects a change in an amount of the reflected light received by the light receiving element (for example, see Japanese Unexamined Patent Application Publication No. H9-89755).

In the detection device according to Japanese Unexamined Patent Application Publication No. H9-89755, the sheet of black paper is provided in a region outside the area irradiated with the light by the light source so as not to allow undesirable light reflected from a background to enter the light receiving element. It is described that the detection device can detect particles of high permeability such as dust as a result of decreasing an amount of the reflected light outside the area irradiated with the light by the light source.

On the other hand, for example, Japanese Unexamined Patent Application No. 2005-140740 discloses a wall surface structure that realizes a visualization space in which micro-particles can be visualized. This visualization space is implemented by further reducing reflected light and scattered light so as to increase visualization sensitivity compared to a visualization space disclosed in Japanese Unexamined Patent Application No. H9-89755, in which a wall surface is simply adapted to be black.

The wall surface structure according to Japanese Unexamined Patent Application No. 2005-140740 includes a wall surface composed of an aggregate of tubular elements (such as honeycomb board). The tubular elements allow at least a portion of the wall to be directed as apertures toward the visualization space in which the suspended particles are visualized with projected light. At least portions of the tubular elements facing the visualization space are adapted to be black.

In the wall surface structure according to Japanese Unexamined Patent Application No. 2005-140740, it is described: The light projected by a light source enters each of the tubular elements, where the light repeats reflection. During the repetition of reflection the absorption and attenuation of the light occurs. The light returns into the visualization space after its energy is sufficiently decreased. In this manner, it is possible to restrict an increase in the intensity of illumination of the visualization space due to reflection and scattering of light, thereby increasing the sensitivity of visualization.

However, it is not practical to employ the wall surface structure according to Japanese Unexamined Patent Application No. 2005-140740, for example, for measuring the cleanliness of a clean room in consideration of cost-effectiveness. It is economical and, therefore, preferable to use a portable particle measurement device for measuring the cleanliness of a clean room as necessary, or periodically.

In addition, Japanese Unexamined Patent Application No. 2005-140740 discloses a portable device in which upper and lower faces are open and an inner wall is surrounded by the tubular elements, and describes that suspended particles can be visualized by installing the portable device where particles are suspended.

However, the abovementioned portable visualization device may have a drawback that it is only able to partially measure suspended particles in a room. On the other hand, a measurement device (portable measurement device) that measures particles by emitting wide-range sheet-like light in a space and detecting reflected light scattered by the particles has already put into practical use. By using such a measurement device, suspended particles in a room can be extensively measured at one time.

On the other hand, the abovementioned measurement device has a drawback to make the measurement of suspended particles with a high sensitivity difficult. The reason for this is that since the emitted light travels substantially straight, the reflected light scattered on wall surfaces, obstacles and suspended particles facing the light source renders a space around a measurement object to be undesirably light.

As a countermeasure against the abovementioned drawbacks, a method of absorbing reflected light by attaching a piece of black paper or a black tape on a wall surface facing a light source can be exemplified, as disclosed in Japanese Unexamined Patent Application Publication No. H9-89755. However, as disclosed in Japanese Unexamined Patent Application Publication No. 2005-140740, there is a limitation to a certain degree for suppressing reflection and scattering of light only by a black reflective surface. In addition, it is often difficult to actually provide a wall surface of a sufficient size in a room.

As another countermeasure against the above-mentioned drawbacks, a method of disposing a screen as disclosed in Japanese Unexamined Patent Application Publication No. 2005-140740 can be exemplified, in which a continuous body of black tubular elements are disposed so as to face a light source. However, although a tubular element disclosed in Japanese Unexamined Patent Application Publication No. 2005-140740 can absorb light obliquely entering an aperture thereof, the tubular element can only partially absorb light entering straight the aperture by a black face disposed at a bottom of the aperture. As a result, it is not possible to expect more from the tubular element than the effects as disclosed in Japanese Unexamined Patent Application Publication No. H9-89755.

Here, suspended particles can be visualized with high sensitivity without being limited by the environment of a room if a device can remove the sheet-like emitted light without being reflected by surfaces facing a light source and obstacles. The above is one of objectives of the present invention.

SUMMARY OF THE INVENTION

Therefore, the present invention provides an apparatus for removing reflected light for visualizing particles suspended in the air with high sensitivity.

In an aspect of the present invention, an apparatus for removing reflected light is provided, which is used for a measuring device that emits a sheet-like beam of light onto suspended particles and measures light scattered from the suspended particles. The apparatus comprises a light introduction unit, a light reflective unit, a light sealing unit and a light absorption member. The light introduction unit has a first aperture shaped like a slit through which the light enters, a second aperture facing the first aperture, and a passage through which the light travels from the first aperture to the second aperture. The light reflective unit that is disposed opposite to the second aperture allows the light having traveled through the second aperture to reflect toward a predetermined direction so as to prevent the light from returning into the second aperture. The light sealing unit in which the light reflective unit is disposed has an inner wall to confine the light reflected from the light reflective unit. The light absorption member is provided on the inner wall of the light sealing unit.

It may be preferable that the light introduction unit has an end portion provided with the first aperture and the end portion projects outwardly from the light sealing unit.

It may be preferable that the light introduction unit has an end portion provided with the second aperture and the end portion projects inwardly into the light sealing unit.

In another aspect of the present invention, an apparatus for removing reflected light is provided, which is used for a measuring device that emits a sheet-like beam of light onto suspended particles and measures light scattered from the suspended particles. The apparatus comprises a light introduction unit, a light absorptive unit, a light sealing unit and a light absorption member. The light introduction unit has a first aperture shaped like a slit through which the light enters, a second aperture facing the first aperture, and a passage through which the light travels from the first aperture to the second aperture. The light absorptive unit that is disposed opposite to the second aperture is irradiated with the light having traveled through the second aperture. The light sealing unit in which the light absorptive unit is disposed has an inner wall to confine the light reflected from the light absorptive unit. The light absorption member is provided on the inner wall of the light sealing unit.

It may be preferable that the light introduction unit has an end portion provided with the first aperture and the end portion projects outwardly from the light sealing unit.

It may be preferable that the light introduction unit has an end portion provided with the second aperture and the end portion projects inwardly into the light sealing unit.

The measuring device includes a light source, an imaging camera, an image processing unit and a main unit. The light source emits the sheet-like beam of light. The imaging camera takes an image of the light scattered by the suspended particles onto which the light is emitted by the light source. The image processing unit receives image data from the imaging camera and converts the light scattered from the suspended particles into data of spot images. The main unit receives the data of spot images from the image processing unit and measures a number of the suspended particles having a predetermined range of particle diameters.

According to the present invention, the apparatus for removing reflected light, which is used for the measuring device that emits the sheet-like beam of light onto the suspended particles and measures the light scattered from the suspended particles, is provided with the light reflective unit. This light reflective unit allows the light having traveled through the second aperture to reflect toward the predetermined direction so as to prevent the light from returning into the second aperture. Since the apparatus introduces the sheet-like beam of light and prevents the reflected light from escaping back to the outside, it is possible to remove the reflected light entering a measurement space. Therefore, the apparatus for removing reflected light according to the present invention can visualize suspended particles with high sensitivity without being affected by the environment conditions of a measurement room.

The apparatus for removing reflected light, which is used for the measuring device that emits the sheet-like beam of light onto the suspended particles and measures the light scattered from the suspended particles, includes the light absorptive unit that is irradiated with the light having entered the passage of the light introduction unit and the light sealing unit with the light absorption member confining the light reflected from the light absorptive unit. Accordingly, it is possible to remove the reflected light. Therefore, the apparatus for removing reflected light according to the present invention can visualize suspended particles with high sensitivity without being affected by the environment conditions of a measurement room.

DETAILED DESCRIPTION OF THE INVENTION

An embodiment of the present invention is described hereinafter with reference to the drawings.

First, a description is provided for an embodiment of a measurement device related to an apparatus for removing reflected light according to the present invention.

Figure 1:
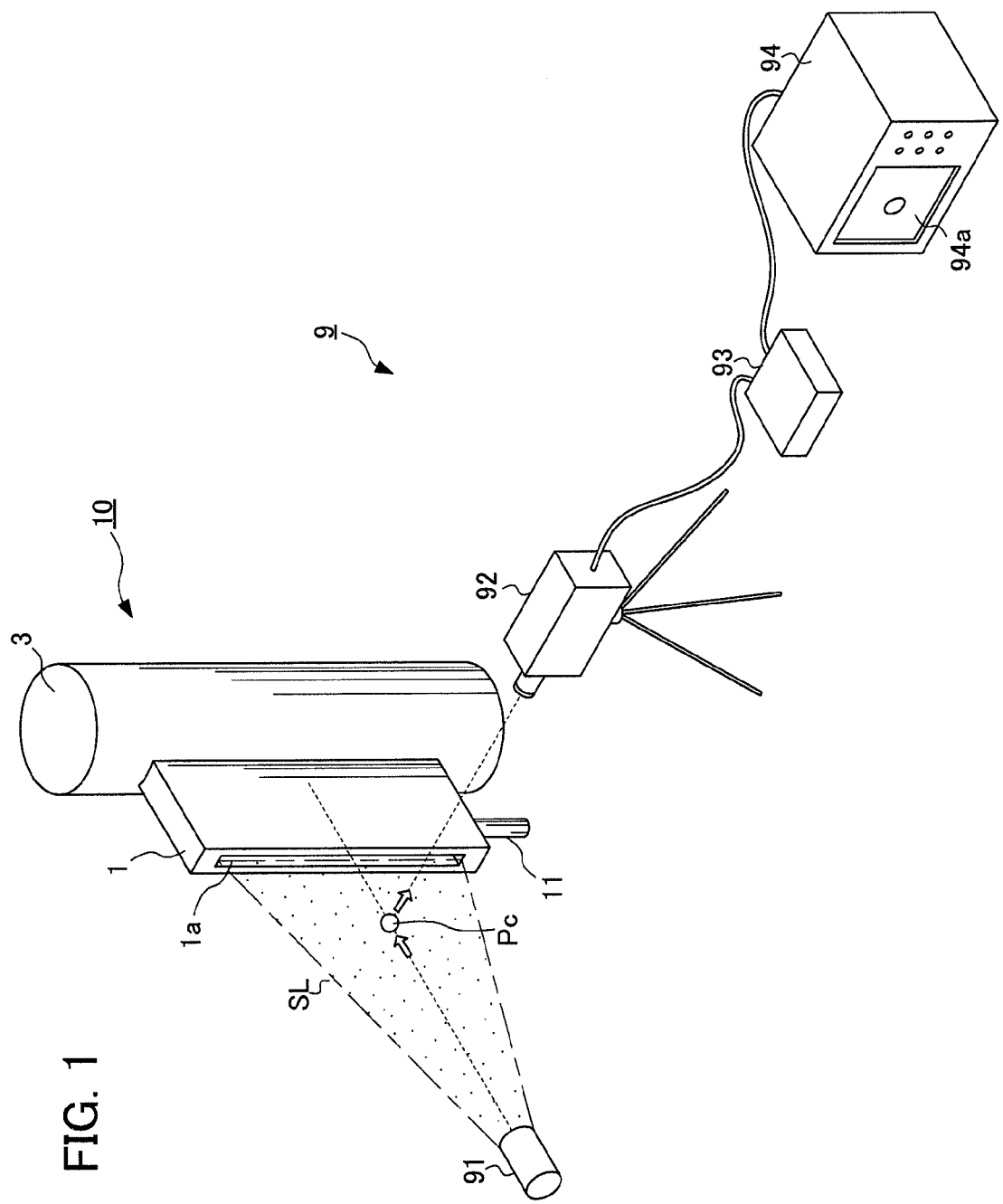
FIG. 1 is a perspective view showing a configuration of an embodiment of a measurement device related to an apparatus for removing reflected light according to the present invention.
Figure 2:
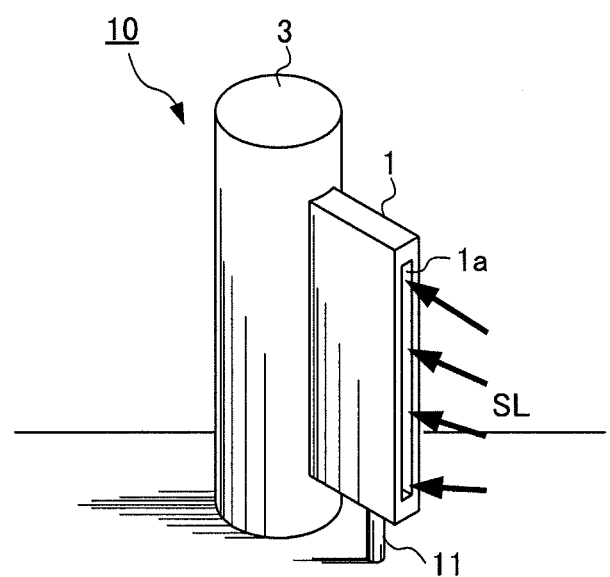
FIG. 2 is a perspective view showing an appearance of the apparatus for removing reflected light according to a first embodiment of the present invention.
Figure 3:
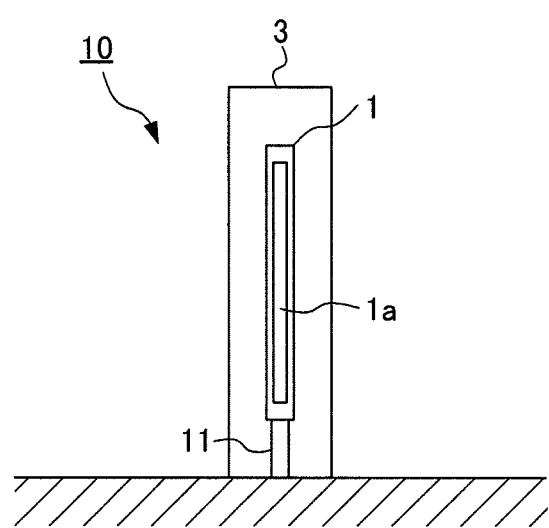
FIG. 3 is a front view of the apparatus for removing reflected light according to the first embodiment.
Figure 4:
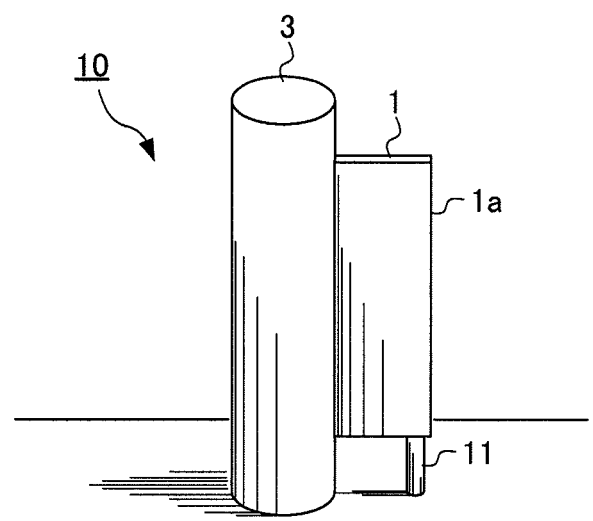
FIG. 4 is a perspective view seen from a left side of the apparatus for removing reflected light according to the first embodiment.

According to FIG. 1, a measurement device 9 is provided with a light source 91 and an imaging camera 92. The light source 91 can emit wide-range sheet-like beam of light (hereinafter referred to as "emitted light") SL. The imaging camera 92 takes an image of scattered light generated by suspended particles Pc irradiated with the emitted light SL by the light source 91. It should be noted that, although the emitted light is laser light in the present embodiment, the emitted light may alternatively be an illuminating light of high luminance.

According to FIG. 1, the measurement device 9 is provided with an image processing unit 93 and a main unit 94. The image processing unit 93 receives image data from the imaging camera 92 and converts the light scattered by the suspended particles Pc into data of spot images. The main unit 94 can measure the number of suspended particles Pc having a predetermined range of particle diameters based on the image data of the suspended particles Pc. The main unit 94 is provided with a monitor screen 94a that displays the image data of the light scattered from the suspended particles Pc obtained by the image processing unit 93. In addition, the main unit 94 is internally provided with a storage device that stores the image data of the light scattered from the suspended particles Pc obtained by the image processing unit 93.

First Embodiment

Next, a description is provided for the apparatus for removing reflected light 10 according to a first embodiment of the present invention.

According to FIGS. 2 to 5, the apparatus for removing reflected light 10 is used for the measuring device 9 that applies the emitted light SL to the suspended particles Pc and measures the light scattered from the suspended particles Pc (see FIG. 1).

According to FIGS. 2 to 5, the apparatus for removing reflected light 10 is provided with a box-like light introduction unit 1. The light introduction unit 1 has a slit-like first aperture 1a through which the emitted light SL enters, a second aperture 1b facing the first aperture 1a, and a passage 1c through which the emitted light SL travels from the first aperture 1a to the second aperture 1b.

According to FIGS. 2 to 5, the apparatus for removing reflected light 10 is provided with a light reflective unit 2 and a first light sealing unit 3 of a cylindrical shape. The light reflective unit 2 is disposed opposite to the second aperture 1b of the light introduction portion 1. The light reflective unit 2 reflects the emitted light SL having passed through the second aperture 1b toward a predetermined direction such that the emitted light SL does not return to the second aperture 1b. The light reflective unit 2 illustrated may be either a triangular prism or a pair of mirrors making an acute angle with each other. An apex of the light reflective unit 2 faces the slit-like second aperture 1b. In addition, the light reflective unit 2 has a length greater than that of the first aperture 1a.

It should be noted that the light reflective unit 2 is not limited to an embodiment such as a triangular prism, a triangular mirror and the like. The light reflective unit 2 may be a flat mirror disposed to be inclined toward the emitted light SL at a predetermined angle or a convex mirror with the apex facing the emitted light SL, provided that such mirrors reflect the emitted light SL toward a predetermined direction such that the emitted light SL does not return to the second aperture 1b.

Figure 5:
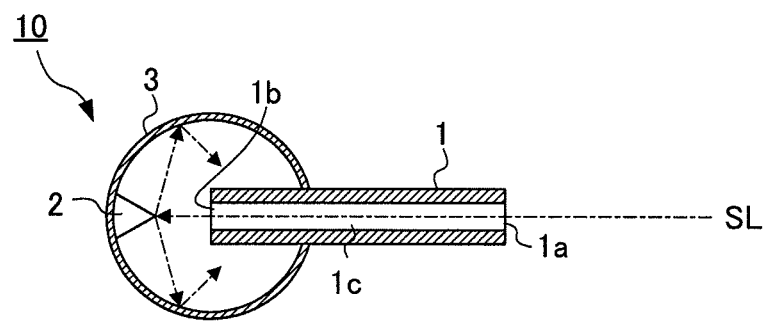
FIG. 5 is a horizontal cross-sectional view of the apparatus for removing reflected light according to the first embodiment.

According to FIG. 5, the first light sealing unit 3 is internally provided with the light reflective unit 2. In addition, an inner wall of the first light sealing unit 3 surrounds the light reflected from the light reflective unit 2. Furthermore, an inner wall of the light introduction unit 1 (an inner wall of the passage 1c) and the inner wall of the first light sealing unit 3 may be either colored in matt black, provided with the surface treatment of fine unevenness, or a combination thereof, which serves as a light absorption member. In other words, the apparatus for removing reflected light 10 is provided with the light absorption member on the inner wall of the first light sealing unit 3.

It should be noted that the light introduction unit 1 and the first light sealing unit 3 may be composed of a black material, have an inner wall colored in black or be attached with a matt black tape. In addition, a colored surface of the black material may be provided with the treatment of fine unevenness (roughness).

According to FIGS. 2 to 5, the light introduction unit 1 has an end portion provided with the first aperture 1a that projects outside from the first light sealing unit 3. In addition, the light introduction unit 1 has an end portion provided with the second aperture 1b that projects inside the first light sealing unit 3. A bottom surface of the first light sealing unit 3 has a predetermined area so as to be able to stand on a floor surface and the like. Furthermore, a support leg 11 is provided at a bottom of the light introduction unit 1.

Next, a description will be provided for the operation of the apparatus for removing reflected light 10 according to the first embodiment of the present invention.

According to FIGS. 2 to 5, with the apparatus for removing reflected light 10, the emitted light SL enters the first aperture 1a. The emitted light SL having passed through the second aperture 1b is reflected by the light reflective unit 2 in such a manner as divided in two directions, so that none of or almost none of the light returns to enter the passage 1c via the second aperture 1b.

According to FIGS. 2 to 5, it is impossible or difficult for the light reflected by the light reflective unit 2 to travel to the passage 1c via the second aperture 1b. The reason for this is that the entirety or almost the entirety of the reflected light is absorbed by the inner wall of the light introduction unit 1 and the inner wall of the first light sealing unit 3, the inner wall being colored in black or provided with the surface treatment of unevenness, which serves as the light absorption member. Therefore, it is impossible or difficult for the emitted light SL having entered the first aperture 1a to be reflected to travel back outside through the first aperture 1a.

As described above, the apparatus for removing reflected light 10 according to the first embodiment of the present invention is disposed to face the emitted light SL coming from the light source 91 so as to remove the reflection of the emitted light SL. In addition, the apparatus for removing reflected light 10 according to the first embodiment of the present invention is portable and can be easily moved.

According to FIGS. 2 to 5, the apparatus for removing reflected light 10 according to the first embodiment has the light reflective unit 2 opposite to the second aperture 1b of the light introduction unit 1 that has the slit-like first aperture 1a through which the emitted light SL enters. The light reflective unit 2 reflects the emitted light SL toward a predetermined direction. Alternatively, the light reflective unit 2 may be integrally formed as a portion of an inner face of the first light sealing unit 3. It may be satisfactory only if the light reflective unit 2 is not a planar surface or a reflective surface perpendicular to the emitted light SL, which allows the emitted light SL to be reflected back into a direction of the light path of the emitted light SL. In addition, the apparatus for removing reflected light 10 is provided with the first light sealing unit 3 that surrounds the light reflected from the light reflective unit 2.

The apparatus for removing reflected light 10 according to the first embodiment introduces the emitted light SL and confines it so as to remove the light that can impinge upon particles suspended in the background air to possibly generate undesirable reflection. As a result of removing the reflected light that intrudes into a visualization space, it is possible to increase the detection sensitivity of the suspended particles Pc within the visualization space.

The measurement of an effect achieved by the apparatus for removing reflected light 10 according to the first embodiment has indicated the following results. With Comparative Example, in which a black tape was attached on a wall surface facing the light source 91 of the measurement device 9, the range of particle diameters of the suspended particles Pc detectable by the measurement device 9 was no less than 50 um. With the apparatus for removing reflected light 10 according to the first embodiment, under the same measurement conditions as described above, the range of particle diameters of the suspended particles Pc detectable by the measurement device 9 was remarkably increased, no less than 0.1 um. It is understood that the detection sensitivity of the suspended particles Pc could be increased as a result of removing the reflected light that intrudes into from the background.

In addition, under the same measurement conditions as described above, the reflected light was compared between two cases: one in which a black tape was used on a wall surface facing the light source 91 (prior art), and the other case in which the apparatus for removing reflected light 10 according to the first embodiment was used. With the prior art, the illuminance of reflected light was measured on a wall surface around the black tape (at a position a few centimeters away from the black tape) and on a floor surface (at a position on the floor surface, a few centimeters away from a point immediately beneath a line of the emitted light SL). With the first embodiment, the illuminance of reflected light was measured on a wall surface around the first light sealing unit 3 (at a position a few centimeters away from the first light sealing unit 3) and on a floor surface (at a position on the floor surface, a few centimeters away from a point immediately beneath a line of the emitted light SL). Positions for measuring the illuminance of reflected light were selected so as not to be directly irradiated with the emitted light SL. The measurement indicates that compared with the black tape, the illuminance of reflected light of which is assumed to be 100, the illuminance of reflected light with the first embodiment was no greater than 1. Therefore, the measurement has demonstrated that the first embodiment is able to provide an effect of removing no less than 99% of the reflected light, compared with the black tape.

Modification of First Embodiment

Next, a description is provided for an apparatus for removing reflected light 20 according to a modification of the first embodiment of the present invention.

Descriptions may be omitted for components bearing the same reference numerals as those used for the explanation of the first embodiment, since these components have the same features as described in the first embodiment. A first light sealing unit 4 shown in FIG. 6 is different from the first light sealing unit 3 of a cylindrical shape only in that the shape of the former is of a quadrangular tube.

Figure 6:
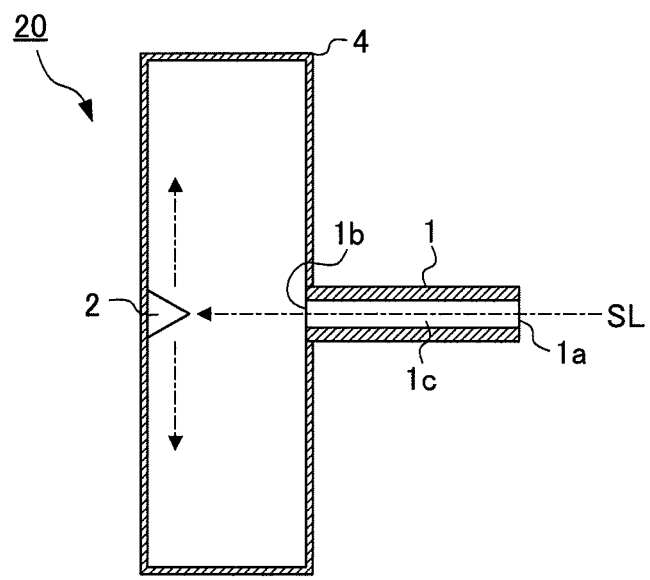
FIG. 6 is a horizontal cross-sectional view of a modification of the apparatus for removing reflected light according to the first embodiment.

According to FIG. 6, the apparatus for removing reflected light 20 is provided with a box-like light introduction unit 1, a light reflective unit 2 and a first light sealing unit 4 shaped in a quadrangular tube. The light introduction unit 1 has a slit-like first aperture 1a through which the emitted light SL enters, a second aperture 1b facing the first aperture 1a, and a passage 1c through which the emitted light SL travels from the first aperture 1a to the second aperture 1b.

According to FIG. 6, the light reflective unit 2 is disposed opposite to the second aperture 1b of the light introduction unit 1. The light reflective unit 2 reflects the emitted light SL having passed through the second aperture 1b toward a predetermined direction such that the emitted light SL does not return to the second aperture 1b. The light reflective unit 2 illustrated may be either a triangular prism or a pair of mirrors making an acute angle with each other. An apex of the light reflective unit 2 faces the slit-like second aperture 1b. In addition, the light reflective unit 2 has a length greater than that of the first aperture 1a.

According to FIG. 6, the first light sealing unit 4 is internally provided with the light reflective unit 2. In addition, the first light sealing unit 4 surrounds the light reflected from the light reflective unit 2. Furthermore, an inner wall of the light introduction unit 1 and the inner wall of the first light sealing unit 4 are colored in black, which serves as a light absorption member.

It should be noted that the light introduction unit 1 and the first light sealing unit 4 may be composed of a black material, have an inner wall colored in black or be attached with a matt black tape.

According to FIG. 6, the light introduction unit 1 has an end portion provided with the first aperture 1a that projects outside from the first light sealing unit 4. In addition, the light introduction unit 1 has an end portion provided with the second aperture 1b that does not project inside the first light sealing unit 4. The second aperture 1b is substantially flush with an inner wall of the first light sealing unit 4. It should be noted that, the present invention is not limited to the embodiment shown in FIG. 6, and the light introduction unit 1 may preferably have an end portion provided with the second aperture 1b projecting deep inside the first light sealing unit 4. In addition, the end portion provided with the second aperture 1b is preferably positioned in the vicinity of the light reflective unit 2, thereby removing more reflected light.

Next, a description is provided for the operation of the apparatus for removing reflected light 20 according to the modification of the first embodiment of the present invention.

According to FIG. 6, with the apparatus for removing reflected light 20, the emitted light SL enters the first aperture 1a. The emitted light SL having passed through the second aperture 1b is reflected by the light reflective unit 2 in such a manner as divided in two directions, so that none of or almost none of the emitted light returns to enter the passage 1c via the second aperture 1b.

According to FIG. 6, it is impossible or difficult for the light reflected by the light reflective unit 2 to travel to the passage 1c via the second aperture 1b. The reason for this is that the entirety or almost the entirety of the reflected light is absorbed by the inner wall of the light introduction unit 1 colored in black, which serves as the light absorption member. Therefore, it is impossible or difficult for the emitted light SL having entered the first aperture 1a to be reflected to travel back outside through the first aperture 1a.

As described above, the apparatus for removing reflected light 20 according to the modification of the first embodiment of the present invention is disposed to face the emitted light SL coming from the light source 91 so as to remove the reflection of the emitted light SL generated in the background. In addition, the apparatus for removing reflected light 20 according to the modification of the first embodiment of the present invention is portable and can be easily moved.

According to FIG. 6, the apparatus for removing reflected light 20 according to the modification of the first embodiment have the light reflective unit 2 opposite to the second aperture 1b of the light introduction unit 1 that has the slit-like first aperture 1a through which the emitted light SL enters. The light reflective unit 2 reflects the emitted light SL toward a predetermined direction. In addition, the apparatus for removing reflected light 20 is provided with the first light sealing unit 4 that surrounds the light reflected from the light reflective unit 2.

The apparatus for removing reflected light 20 according to the modification of the first embodiment introduces the emitted light SL and confines it so as to remove the light that can impinge upon particles suspended in the background air to possibly generate reflection. In this manner, this apparatus removes the reflected light that may intrude into the observation space (measurement space) for suspended particles in the air. As a result of removing the reflected light that intrudes into a visualization space, it is possible to increase the detection sensitivity of the suspended particles Pc within the visualization space.

Second Embodiment

Next, a description is provided for an apparatus for removing reflected light 30 according to a second embodiment of the present invention.

Figure 7:
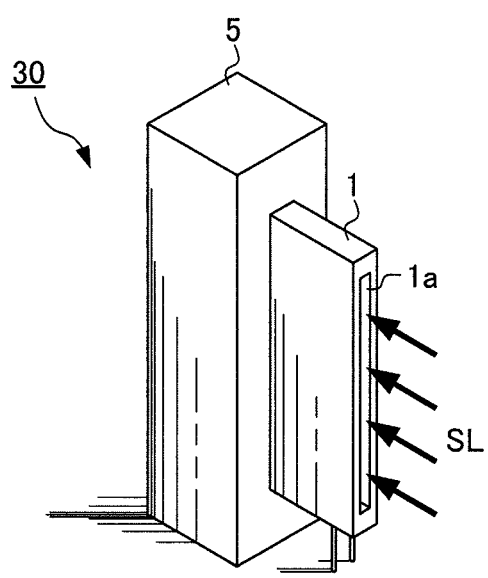
FIG. 7 is a perspective view showing an appearance of the apparatus for removing reflected light according to a second embodiment of the present invention.
Figure 8:
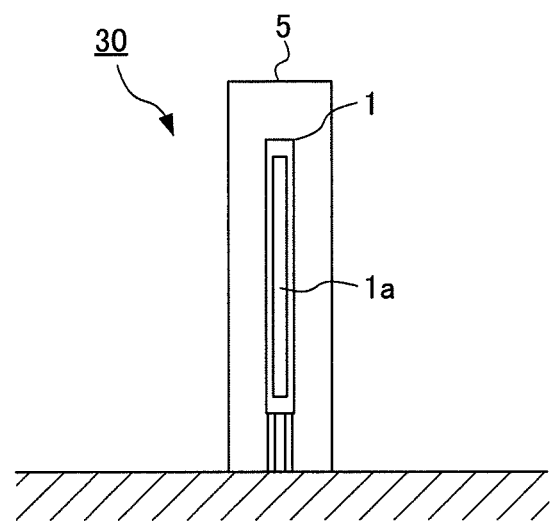
FIG. 8 is a front view of the apparatus for removing reflected light according to the second embodiment.
Figure 9:
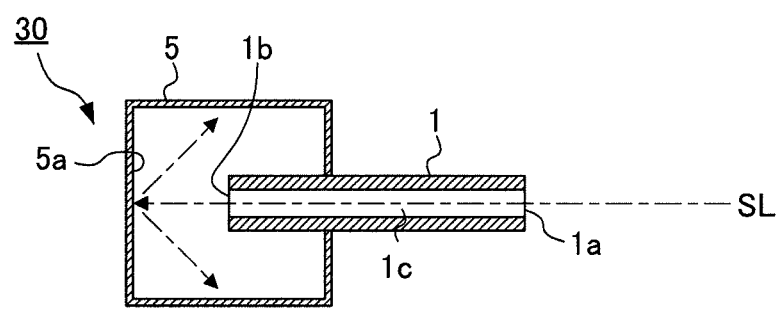
FIG. 9 is a horizontal cross-sectional view of the apparatus for removing reflected light according to the second embodiment.

According to FIGS. 7 to 9, the apparatus for removing reflected light 30 is used for a measuring device 9 that applies the emitted light SL to suspended particles Pc and measures the light scattered from the suspended particles Pc (see FIG. 1).

According to FIGS. 7 to 9, the apparatus for removing reflected light 30 is provided with a box-like light introduction unit 1, a light absorptive unit 5a and a second light sealing unit 5 that is shaped in a quadrangular tube. The light introduction unit 1 has a slit-like first aperture 1a through which the emitted light SL is incident, a second aperture 1b facing the first aperture 1a, and a passage 1c through which the emitted light SL passes from the first aperture 1a to the second aperture 1b.

According to FIG. 9, the light absorptive unit 5a is opposite to the second aperture 1b of the light introduction unit 1. The emitted light SL having passed through the second aperture 1b is perpendicularly incident on the light absorptive unit 5a. The light absorptive unit 5a forms one of inner walls of the second light sealing unit 5. In addition, the light absorptive unit 5a has a length greater than that of the first aperture 1a.

According to FIG. 9, the second light sealing unit 5 is internally provided with the light absorptive unit 5a. An inner wall of the second light sealing unit 5 surrounds the light reflected from the light absorptive unit 5a. Inner walls of the light introduction unit 1 and the second light sealing unit 5 are colored in black for light absorption. In other words, the apparatus for removing reflected light 30 has a light absorption member on the inner wall of the second light sealing unit 5.

It should be noted that the light introduction unit 1 and the second light sealing unit 5 may be composed of a black material, have an inner wall colored in black or be attached with a matt black tape. In addition, the light absorption member of the inner walls of the light introduction unit 1 and the second light sealing unit 5 may be provided with the surface treatment of fine unevenness.

According to FIG. 9, the light introduction unit 1 has an end portion provided with the first aperture 1a that projects outside from the second light sealing unit 5. In addition, the light introduction unit 1 has an end portion provided with the second aperture 1b that projects inside the second light sealing unit 5.

Next, a description is provided for the operation of the apparatus for removing reflected light 30 according to the second embodiment of the present invention.

According to FIGS. 7 to 9, with the apparatus for removing reflected light 30, the emitted light SL enters the first aperture 1a. The emitted light SL having passed through the second aperture 1b is absorbed by the light absorptive unit 5a, so that none of or almost none of the emitted light SL returns to enter the passage 1c via the second aperture 1b.

According to FIG. 9, it is impossible or difficult for the light reflected by the light absorptive unit 5a to travel to the passage 1c via the second aperture 1b. The reason for this is that the entirety or almost the entirety of the reflected light is absorbed by the inner wall of the second light sealing unit 5, the inner wall being colored in black, which serves as the light absorption member. Therefore, it is impossible or difficult for the emitted light SL having entered the first aperture 1a to be reflected to travel back outside through the first aperture 1a.

As described above, the apparatus for removing reflected light 30 according to the second embodiment of the present invention is disposed to face the emitted light SL coming from the light source 91 so as to remove the reflection of the emitted light SL from the background. In addition, the apparatus for removing reflected light 30 according to the second embodiment of the present invention is portable and can be easily moved.

According to FIGS. 7 to 9, the apparatus for removing reflected light 30 according to the second embodiment has the light absorptive unit 5a opposite to the second aperture 1b of the light introduction unit 1 that has the slit-like first aperture 1a through which the emitted light SL enters. In addition, the apparatus for removing reflected light 30 is provided with the second light sealing unit 5 that surrounds the light reflected from the light absorptive unit 5a.

The apparatus for removing reflected light 30 according to the second embodiment introduces the emitted light SL and confines it so as to remove the light that can impinge upon particles suspended in the background air to possibly generate reflection. As a result of removing the reflected light that intrudes into a visualization space, it is possible to increase the detection sensitivity of the suspended particles Pc within the visualization space.

In this manner, a system for visualizing suspended particles can be implemented using the apparatus for removing reflected light and the measurement device according to the embodiments of the present invention.

The system for visualizing suspended particles can capture an instantaneous phenomenon such as dust occurring by chance. The system for visualizing suspended particles can also capture a local phenomenon such as dust occurring only in a certain location. Furthermore, the system for visualizing suspended particles allows intuitive recognition of behavior of dust and particles.

What is claimed is:

1. An apparatus for removing reflected light used for a measuring device that emits a sheet-like beam of light onto suspended particles and measures light scattered from the suspended particles, the apparatus comprising:
   a light introduction unit having a first aperture shaped like a slit through which the light enters, a second aperture facing the first aperture, and a passage through which the light travels from the first aperture to the second aperture;
   a light reflective unit that is disposed opposite to the second aperture allowing the light having traveled through the second aperture to reflect toward a predetermined direction so as to prevent the light from returning into the second aperture;

a light sealing unit in which the light reflective unit is disposed having an inner wall to confine the light reflected from the light reflective unit; and a light absorption member provided on the inner wall of the light sealing unit, wherein the sheet-like beam of light traverses the suspended particles prior to entering the first aperture, forming a sheet-like measurement space having one edge at an entrance of the first aperture, and wherein the measuring device measures the light scattered from the suspended particles in the sheet-like measurement space.

2. The apparatus according to claim 1, wherein the light introduction unit has an end portion provided with the first aperture, the end portion projecting outwardly from the light sealing unit.

3. The apparatus according to claim 1, wherein the light introduction unit has an end portion provided with the second aperture, the end portion projecting inwardly into the light sealing unit.

4. The apparatus according to claim 1, wherein the measuring device includes:

a light source emitting the sheet-like beam of light; an imaging camera taking an image of the light scattered from the suspended particles onto which the light is emitted by the light source;

an image processing unit receiving image data from the imaging camera and converting the light scattered from the suspended particles into data of spot images; and a main unit receiving the data of spot images from the image processing unit and measuring a number of the suspended particles having a predetermined range of particle diameters.

5. An apparatus for removing reflected light used for a measuring device that emits a sheet-like beam of light onto suspended particles and measures light scattered from the suspended particles, the apparatus comprising:

a light introduction unit having a first aperture shaped like a slit through which the light enters, a second aperture facing the first aperture, and a passage through which the light travels from the first aperture to the second aperture;

a light absorptive unit disposed opposite to the second aperture, the light absorptive unit being irradiated with the light having traveled through the second aperture;

a light sealing unit in which the light absorptive unit is disposed having an inner wall to confine the light reflected from the light absorptive unit; and a light absorption member provided on the inner wall of the light sealing unit, wherein the sheet-like beam of light traverses the suspended particles prior to entering the first aperture, forming a sheet-like measurement space having one edge at an entrance of the first aperture, and wherein the measuring device measures the light scattered from the suspended particles in the sheet-like measurement space.

6. The apparatus according to claim 5, wherein the light introduction unit has an end portion provided with the first aperture, the end portion projecting outwardly from the light sealing unit.

7. The apparatus according to claim 5, wherein the light introduction unit has an end portion provided with the second aperture, the end portion projecting inwardly into the light sealing unit.

8. The apparatus according to claim 5, wherein the measuring device includes:

a light source emitting the sheet-like beam of light;

an imaging camera taking an image of the light scattered by the suspended particles onto which the light is emitted by the light source;

an image processing unit receiving image data from the imaging camera and converting the light scattered from the suspended particles into data of spot images; and a main unit receiving the data of spot images from the image processing unit and measuring a number of the suspended particles having a predetermined range of particle diameters.

* * * * *